United States Patent [19]

Bauerfeind et al.

[11] Patent Number: 5,393,300
[45] Date of Patent: Feb. 28, 1995

[54] SHOULDER JOINT BANDAGE

[75] Inventors: Hans B. Bauerfeind, Kempen; Rainer Scheuermann, Kiel, both of Germany

[73] Assignee: Bauerfeind GmbH & Co., Germany

[21] Appl. No.: 78,586

[22] Filed: Jun. 17, 1993

[30] Foreign Application Priority Data

Jul. 1, 1992 [DE] Germany ............................ 4221502

[51] Int. Cl.6 ............................................... A61F 5/00
[52] U.S. Cl. ........................................ 602/4; 602/19; 602/62; 128/DIG. 19; 128/876; 128/878
[58] Field of Search ...................... 602/4, 5, 12, 19, 20, 602/53, 60–62; 2/44, 45, 92; 128/DIG. 19, 869, 876, 878, 881

[56] References Cited

U.S. PATENT DOCUMENTS

| | | | |
|---|---|---|---|
| 4,188,944 | 2/1980 | Augustyniak | 602/20 |
| 4,198,964 | 4/1980 | Honneffer | 602/19 |
| 4,446,858 | 5/1984 | Verter | 602/4 |
| 4,598,703 | 7/1986 | Lindemann | 602/4 |
| 4,735,198 | 4/1988 | Sawa | 2/44 X |
| 4,751,923 | 6/1988 | Marino | 602/4 |
| 4,784,128 | 11/1988 | Scheuermann | 2/45 X |
| 4,844,306 | 7/1989 | Ruff et al. | 602/4 X |
| 4,905,713 | 3/1990 | Morante | 602/20 X |
| 5,018,513 | 5/1991 | Charles | 602/19 |
| 5,188,587 | 2/1993 | McGuire et al. | 602/20 |

*Primary Examiner*—Richard J. Apley
*Assistant Examiner*—Linda C. M. Dvorak

[57] ABSTRACT

Shoulder joint bandage with a tubular section which envelops the upper arm and a shoulder top piece connecting thereto to whose edge on the neck side retaining straps are fastened of which one—in the form of a back strap—traverses the back diagonally and envelops the hip under the armpit of the shoulder which is opposite to the shoulder top piece whereas the other is led at least partially—in the form of a chest strap—over the side of the chest to this hip where the back strap and chest strap cross and continue in their direction, in each case, on the other side of the body into the other half of the body. The two continuation belts at the upper arm located near the hip in question envelop this in the opposite direction from the hip side whereby the end of each continuation belt is attached, in each case, to the same continuation belt after enveloping the upper arm.

8 Claims, 2 Drawing Sheets

SHOULDER JOINT BANDAGE

FIELD OF THE INVENTION

The invention relates to a shoulder joint bandage with a tubular section which envelops the upper arm and a shoulder top piece connected thereto. Two retaining straps are fastened on the neck side of the edge in the form of a back strap, one of which traverses the back diagonally and envelops the hip under the armpit of the shoulder which is opposite to the shoulder top piece, whereas the other is led at least partially in the form of a chest strap over the side of the chest to the hip where the back strap and chest strap cross and continue in their directions, in each case, on the other side of the body into the other half of the body.

DESCRIPTION OF THE PRIOR ART

Such a shoulder joint bandage is known from DE German GBM 90 10 801.9 and German patent specification 37 04 288. This shoulder bandage serves the purpose of bandaging an injured shoulder in terms of after-treatment for operative incursions at the shoulder joint and in order to relieve pain and to assist the healing process whereby the shoulder joint retains considerable latitude for movement.

SUMMARY OF THE INVENTION

The present invention involves redesigning known shoulder joint bandages so that in contrast to the target direction pursued in known shoulder joint bandages, healing is provided by positioning the shoulder joint at rest. In accordance with the invention, such resting is provided by two continuation belts at the upper arm located near the hip in question which envelop the arm in the opposite direction from the hip side whereby the end of each continuation belt is attached, in each case, to the same continuation belt after enveloping the upper arm.

The continuation belts are joined to one another in the case of known shoulder joint bandages to exert a certain tension as a result of counter-enveloping the upper arm to pull to the side of the body in question both in the direction toward the front and to the rear whereby these forces compensate each other mutually because of envelopment of the upper arm both from the side of the chest and from the side of the back and do not materialize in the form of a tension for the upper arm. Because of mutual envelopment, the mutual fixation of the continuation belts also remains intact in this way although their ends are attached at the same continuation belt since each tensile force acting in the continuation belt is taken up via the fixed upper arm by the other continuation belt in each case. In order to facilitate the attachment of the shoulder joint bandage and to make possible adaptation to different circumferences of the arm, this is expediently designed so that the tubular section is slit longitudinally to facilitate the accommodation of the upper arm and overlapping straps are arranged with a loop and hook detachable closure device along the slit which, in each case, overlap the other side.

In order to stabilize the two retaining straps with regard to their mutual position traversing the back or, as the case may be the chest, the two retaining straps can be held mutually in a buckle at their crossing location and in a manner in which they are capable of displacement relative to the buckle. As a result of the ability of each individual retaining strap to be displaced, the position of the buckle can be adjusted in a simple manner in the region of the hip that is opposite to the shoulder top piece so that adequate lengths result for the length of the continuation belts and their envelopment of the upper arm.

The ends of the continuation belts are expediently provided with a loop and hook detachable closure device to attach the ends of the continuation belts to themselves. In this case, the shoulder joint bandage is expediently formed from fleece-like material whereby the ends of the continuation belts are provided with the hook portion of the fastener on the straps.

In order to be fixed reliably onto the lower arm, a sling can be provided to accommodate the lower arm. The sling is wound around the continuation of the retaining strap in question on the side of the abdomen. Since the continuation belt on the side of the abdomen from the crossing location to the enveloped upper arm is firmly located at the abdomen, the sling is also held firmly as a result of which an arm which is being carried by the sling is also fixed firmly.

In order to give the patient the possibility of being able to move and to re-fix the forearm in accordance with the nature of the treatment, the sling is expediently designed in such a way that it is formed from a web whose ends are joined together by means of a hook and loop closure device. On opening the closure device, the sling can readily be taken off and this thereby gives mobility to the forearm above the elbow joint. The underarm is then fixed again by applying the sling.

One form of embodiment of the invention is given in the Figures. The following aspects are shown.

DESCRIPTION OF THE PREFERRED EMBODIMENTS

Figure 1:
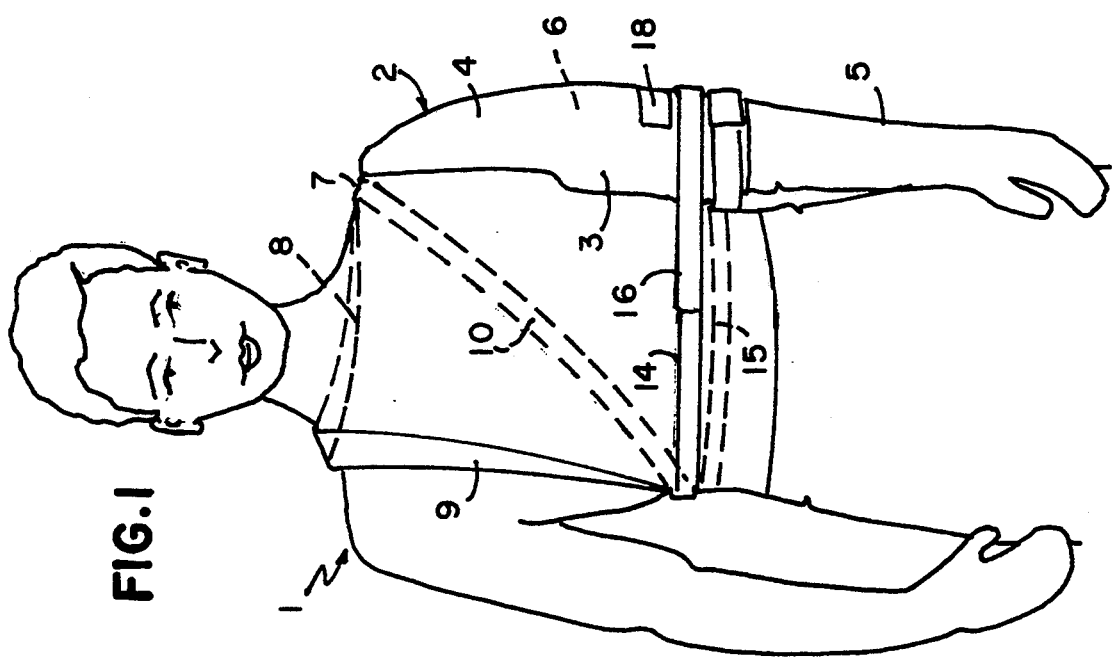
FIG. 1 shows the front view of a patient with a shoulder joint bandage attached which has a tubular section and an adjoining shoulder top piece.
Figure 2:
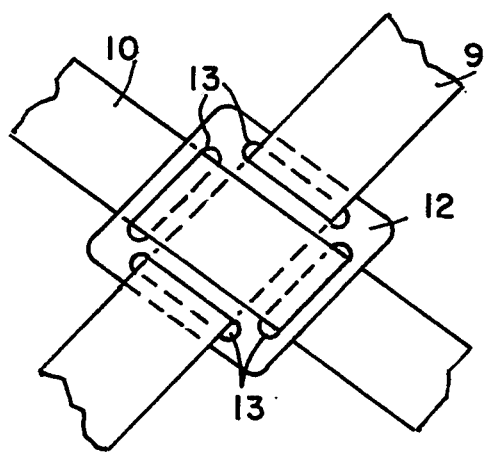
FIG. 2 shows a buckle which is contained in the bandage.

FIG. 1 shows a patient with an attached shoulder joint bandage 2 which contains the shoulder top piece 4. The shoulder top piece 4 lies fully around the shoulder of the patient 1 and envelops his upper arm via its tubular section 3. In order to pull on the shoulder joint bandage 2, the forearm 5 is placed through the tubular section 3 until it reaches in the region of the upper arm 6 whereby the shoulder top piece, which is open toward the inside, envelops the shoulder. In order to provide the shoulder joint bandage 2 with a particular position on the body of the patient 1, two retaining straps are provided which are attached jointly to the edge of the shoulder top piece 4, at the attachment location 7, which is turned toward the neck. A retaining strap 8 runs from the attachment location 7 below the nape of the neck of the patient 1 to the shoulder of the patient which lies opposite the shoulder top piece 4 where it goes over into the chest strap 9. The other retaining strap runs from the attachment location 7 in the form of a back retaining strap 10 which runs diagonally over the back to the hip which lies opposite the tubular section 3 where the back strap 10 and the chest strap 9 cross. A buckle is provided at this crossing location 11 which is represented as 12 in FIG. 2 through which the crossing straps i.e. the back strap 10 and the chest strap 9 are mutually held. The buckle 12 is provided with four elongated holes 13 whereby, in each case, opposite elongated holes serve for threading through one strap in each case. As a result of this, assurance is provided that each strap can be individually pushed through the buckle 12 so that the buckle 12 remains capable of being displaced relative to each strap.

From the crossing location 11, the back strap 10 continues in a continuation belt 14. Here, the chest strap 9 extends into a continuation belt 15. Holding the upper arm 6 in a restful position is brought about by these two continuation belts in the following way. The continuation belt 14, which runs over the abdomen of the patient 1, re-encircles the tubular section 3 from the rear and after encircling it on the front it is fixed into position. In the corresponding manner, the continuation belt 15 which runs over the back passes between the body of the patient 1 and the upper arm 6 and thus encircles the tubular section 6 from the front after which the end in question of the continuation belt 14 is attached to this on the side of the back of the patient. In this way, the upper arm 6 of the patient 1 is retained by two loops running counter to one another which, on the one hand, draw the upper arm 6 to the body of the patient 1 and, on the other hand, prevent the patient from carrying out a swinging movement with his upper arm 6. The upper arm 6 is securely held in its original position by the two encirclements of the upper arm 6 via the extensions 14 and 15 with mutual cancellation of possible tensile forces.

Figure 3:
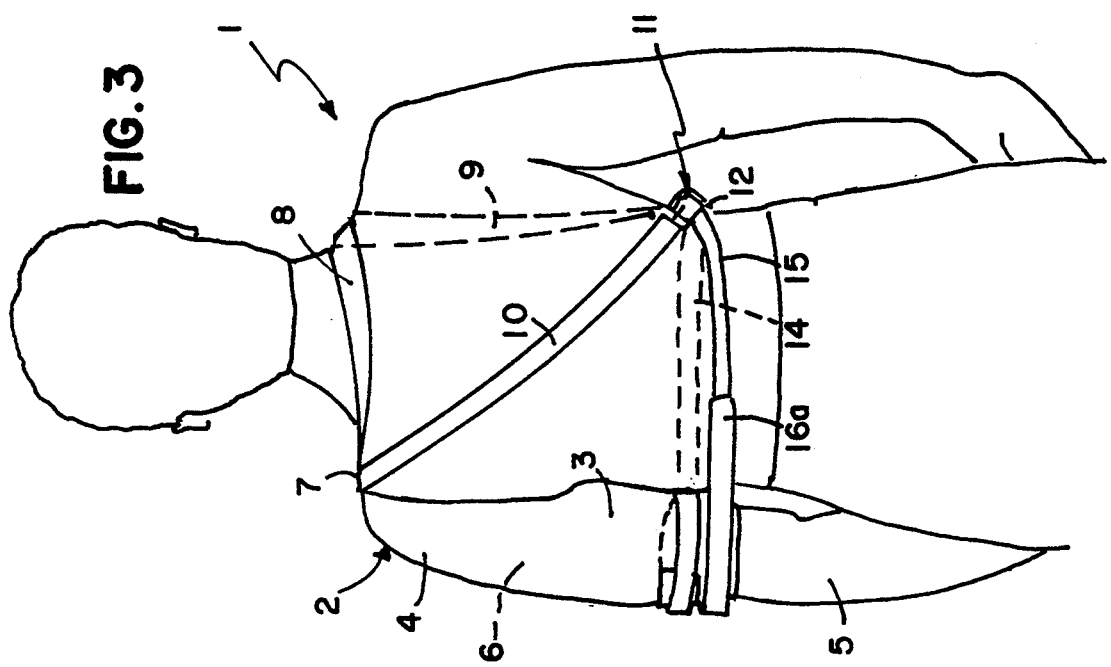
FIG. 3 shows the rear view of a patient.

FIG. 3 shows the rear view of the patient 1 from which the positioning of the two retaining straps over the back can be seen. The shoulder top piece 4 and the tubular section 3 are again shown as well as one retaining strap 8 which runs in the region of the nape of the neck of the patient 1 from the attachment position 7 to the shoulder of the patient opposite the shoulder top piece 4 and goes over here into the chest strap 9 which is drawn in the form of broken lines. The back strap 10 runs from the attachment location 7 diagonally over the back of the patient 1 and meets the chest strap 9 in the crossing location 11. The continuation belt 14 of the back strap 10 runs from this crossing location over the abdomen of the patient 1 whereas the continuation belt 15 of the chest strap 9 runs over the back of the patient 1. The continuation belts 14 and 15 then encircle the tubular section 3 in the region of the tubular section 3 and this is done in such a way that the continuation belt 14 passes between the tubular section and the body of the patient 1 from the side of the abdomen to the rear in order to encircle the tubular section 3 on the side of the back of the patient 1 after which the continuation belt 14 is attached by its end 16 at the continuation belt 14. Conversely, the continuation belt 15 passes from the back of the patient 1 between his body and the tubular section 3 toward the front in order to encircle the tubular section 3 after which the continuation belt 15 is then attached on the front side around the tubular section and is attached by its end 16a to the continuation belt 15.

Figure 4:
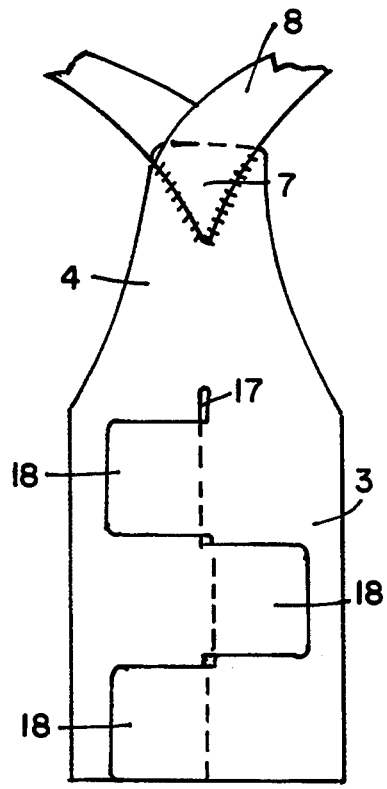
FIG. 4 shows the side view of the shoulder top piece.

FIG. 4 shows the shoulder top piece 4 and the tubular section 3 alone. The tubular section 3 is provided here with a longitudinal slit 17 which can be opened in order to facilitate the application of the shoulder joint bandage. In order to close the tubular section 3, straps 18 are provided which alternately overlap the slit 17 and are designed in such a way in the form of a hook and loop closure device that this is closed by pressing the straps 18 against the material of the tubular section 17.

Figure 5:
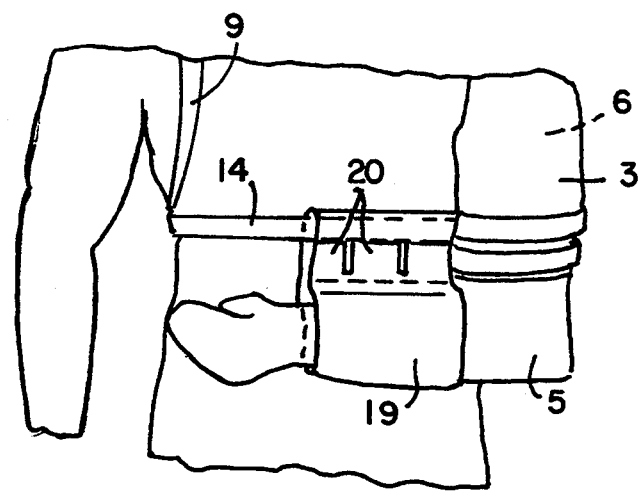
FIG. 5 shows the front view of a patient with the sling which carries the underarm.

The sling 19 is shown in FIG. 5 and serves to hold the forearm in a resting position and is wound around the continuation belt 14 which runs on the side of the abdomen. The sling 19 thus hangs to a certain extent on the continuation belt 14. In the case of a forearm 5 inserted into the sling 19, this is held in such a way that it can virtually not be moved. This also depends on the tightness of the encirclement of the forearm 5 by the sling 19. In order that the sling 19 be capable of being applied with ease, it is designed in the form of a strap which is held together by its ends via overlapping hook and loop closure devices. The hook and loop closure devices are opened in order to slide in the forearm 5 after which the strap in question can be wound around the forearm in the form of a sling after which the sling is applied firmly around the forearm 5 by closing the hook and loop closure devices 20 and, in this way, keeps it in position.

In order to design, in a favorable manner, the hook and loop closure devices which are used and the attachment to the ends of the two continuation belts 14 and 15, the shoulder joint bandage is itself made from a fleece-like material which can then work in conjunction with the hook parts of the closure devices 20 or, as the case may be, the straps 18. In a corresponding manner, the ends of the extensions 14 and 15 can be provided with the hook portion of a hook and loop fastener which then firmly hooks into the fleece material of the extension in question.

While it is apparent that changes and modifications can be made within the spirit and scope of the present invention, it is our intention only to be limited by the appended claims.

As our invention we claim:

1. A shoulder joint bandage (2) with a tubular section (3) adapted to envelop the upper arm (6), said tubular section having a shoulder top piece (4) connected thereto, said top piece having an edge, said edge being disposed on the neck side and having retaining straps (8, 10) fastened thereto, one of which is in the form of a back strap (10) adapted to traverse the back diagonally and envelop the hip under the armpit of the shoulder which is opposite to the shoulder having said top piece (4) disposed thereon and the other of which is adapted to be disposed at least partially in the form of a chest strap (9) over the side of the chest to said hip where the back strap and chest strap (9, 10) cross and continue in their directions, in each case, on the other side of the body into the other hip of the body, characterized by the feature of two continuation belts (14, 15) adapted to hold the upper arm (6) adjacent said hip, one of said continuation belts extending from said back strap and the other of said continuation belts extending from said chest strap, one of said continuation belts being adapted to encircle said upper arm in one direction and the other of said continuation belts being adapted to encircle the arm in the opposite direction, each of said belts being arranged to connect to itself to secure the upper arm adjacent said hip.

2. The shoulder joint bandage in accordance with claim 1, characterized by the feature that in order to facilitate the accommodation of the upper arm (6), the tubular section (3) is slit longitudinally and overlapping straps (18) are arranged with a hook and loop closure device along the slit (17) alternatively overlap the opposite side.

3. Shoulder joint bandage in accordance with claim 1, characterized by the feature that the two retaining straps (8, 10) can be held mutually in a buckle (12) at the location (11) in which they cross and in a manner in which they are capable of displacement relative to the buckle (12).

4. Shoulder joint bandage in accordance with claim 2, characterized by the feature that the two retaining straps (8, 10) can be held mutually in a buckle (12) at the location (11) in which they cross and in a manner in which they are capable of displacement relative to the buckle (12).

5. Shoulder joint bandage in accordance with claim 1, characterized by the feature that the ends (16) of the continuation belts (14, 15) are attached to these by means of a hook and loop closure device.

6. Shoulder joint bandage in accordance with claim 4, characterized by the feature that it consists of a fleece-like material and the ends (16) of the continuation belts (14, 15) are provided with the hook portion of a hook and loop fastener.

7. The shoulder joint bandage in accordance with claim 1, characterized by the feature that a sling (19) is wound around the continuation belt (14) on the side of the abdomen and serves to accommodate the forearm (5).

8. Shoulder joint bandage in accordance with claim 6, characterized by the feature that the sling (19) is formed from strapping whose ends are joined together by means of a hook and loop closure device (20).

* * * * *